United States Patent
Wang et al.

(10) Patent No.: US 12,262,983 B2
(45) Date of Patent: Apr. 1, 2025

(54) SYSTEM AND METHOD FOR DETECTING SMALL BLOOD-TISSUE BARRIER DISRUPTION

(71) Applicants: UNIVERSITY OF CINCINNATI, Cincinnati, OH (US); CHILDREN'S HOSPITAL MEDICAL CENTER, Cincinnati, OH (US)

(72) Inventors: Jinghua Wang, Mason, OH (US); Lili He, Mason, OH (US)

(73) Assignees: University of Cincinnati, Cincinnati, OH (US); Children's Hospital Medical Center, Cincinnati, OH (US)

(*) Notice: Subject to any disclaimer, the term of this patent is extended or adjusted under 35 U.S.C. 154(b) by 609 days.

(21) Appl. No.: 16/968,231

(22) PCT Filed: Feb. 7, 2019

(86) PCT No.: PCT/US2019/016954
§ 371 (c)(1),
(2) Date: Aug. 7, 2020

(87) PCT Pub. No.: WO2019/157119
PCT Pub. Date: Aug. 15, 2019

(65) Prior Publication Data
US 2021/0030301 A1    Feb. 4, 2021

Related U.S. Application Data

(60) Provisional application No. 62/627,369, filed on Feb. 7, 2018.

(51) Int. Cl.
*A61B 5/055* (2006.01)
*A61B 5/00* (2006.01)
*G01R 33/56* (2006.01)

(52) U.S. Cl.
CPC ............ *A61B 5/055* (2013.01); *A61B 5/0042* (2013.01); *G01R 33/5601* (2013.01)

(58) Field of Classification Search
CPC ..... A61B 5/055; A61B 5/0042; A61B 5/4064; A61B 5/4076–4088; G01R 33/5601
See application file for complete search history.

(56) References Cited

U.S. PATENT DOCUMENTS

| | | | |
|---|---|---|---|
| 9,046,589 B2 | 6/2015 | Gjesdal et al. | |
| 9,194,867 B2 | 11/2015 | Vojdani | |

(Continued)

FOREIGN PATENT DOCUMENTS

| | | | | |
|---|---|---|---|---|
| AU | 2014202211 B2 | * | 6/2016 | ............. A61K 31/10 |
| CN | 102947305 B | * | 7/2016 | ................ A61P 1/00 |

(Continued)

OTHER PUBLICATIONS

The impact of increased mean airway pressure on contrast-enhanced MRI measurement of regional cerebral blood flow (rCBF), regional cerebral blood volume (rCBV),(rMTT), and regional cerebrovascular resistance (rCVR) in human volunteers Christian Kolbitsch,Ingo H. Lorenz,Chri (Year: 2000).*

(Continued)

*Primary Examiner* — Keith M Raymond
*Assistant Examiner* — Fikirte (Fiki) T Ashine
(74) *Attorney, Agent, or Firm* — Dinsmore & Shohl LLP

(57) ABSTRACT

A method for detecting blood-tissue barrier breakdown or disruption is provided. The method includes acquiring first image data of a target region of a subject with a predetermined spatial resolution; administrating exogenous or endogenous tracer into the subject; acquiring second image data of the target region with the predetermined spatial resolution after administration of the tracer; differentiating healthy tissue and pathological tissue with blood-tissue (Continued)

barrier breakdown in the target region based on the first image data and the second image data; and visualizing or analyzing the blood-tissue barrier breakdown of pathological tissue based on the differentiation.

16 Claims, 7 Drawing Sheets

(56) References Cited

U.S. PATENT DOCUMENTS

| | | | |
|---|---|---|---|
| 9,291,692 B2 | 3/2016 | Yang et al. | |
| 9,599,625 B2 | 3/2017 | Liu et al. | |
| 9,913,899 B2 | 3/2018 | Kauvar et al. | |
| 10,076,263 B2 | 9/2018 | Leigh et al. | |
| 2003/0095693 A1* | 5/2003 | Kaufman | G06T 5/20 |
| | | | 382/280 |
| 2012/0179028 A1 | 7/2012 | Caravan et al. | |
| 2013/0335083 A1* | 12/2013 | Wasserman | G01R 33/4806 |
| | | | 324/309 |
| 2014/0086827 A1 | 3/2014 | Janigro et al. | |
| 2014/0294734 A1* | 10/2014 | Gulani | G01R 33/56 |
| | | | 324/309 |
| 2015/0018665 A1* | 1/2015 | Jasanoff | C07K 14/585 |
| | | | 600/407 |
| 2015/0065865 A1* | 3/2015 | Leigh | A61B 5/055 |
| | | | 600/420 |
| 2015/0141804 A1 | 5/2015 | Rooney et al. | |
| 2015/0265210 A1 | 9/2015 | Israeli et al. | |
| 2016/0000945 A1* | 1/2016 | Nedergaard | A61K 31/41 |
| | | | 424/1.73 |
| 2016/0109539 A1* | 4/2016 | Mardor | A61B 5/7275 |
| | | | 600/420 |
| 2016/0120893 A1 | 5/2016 | Gu et al. | |
| 2017/0247429 A1 | 8/2017 | Cooper et al. | |
| 2018/0169274 A1* | 6/2018 | Berger | C07D 257/02 |
| 2018/0250361 A1 | 9/2018 | Monnier et al. | |
| 2018/0256756 A1 | 9/2018 | Kopke et al. | |
| 2019/0350486 A1* | 11/2019 | Walczak | A61M 5/14 |

FOREIGN PATENT DOCUMENTS

| | | |
|---|---|---|
| JP | 2016516523 A * | 6/2016 |
| WO | 2017021951 A1 | 2/2017 |

OTHER PUBLICATIONS

Lin, W., Paczynski, R. P., Kuppusamy, K., Hsu, C. Y., and Haacke, E. M. (1997) Quantitative measurements of regional cerebral blood volume using MRI in rats: Effects of arterial carbon dioxide tension and mannitol. Magn. Reson. Med. 38, 420-428. Dec. 12, 2005 (Year: 2005).*

Price, L.; Wilson, C.; Grant, A.G. Blood-brain barrier pathophysiology following traumatic brain injury. In Translational Research in Traumatic Brain Injury; CRC Press: Boca Raton, FL, USA, 2015; pp. 85-96. [ (Year: 2015).*

* cited by examiner

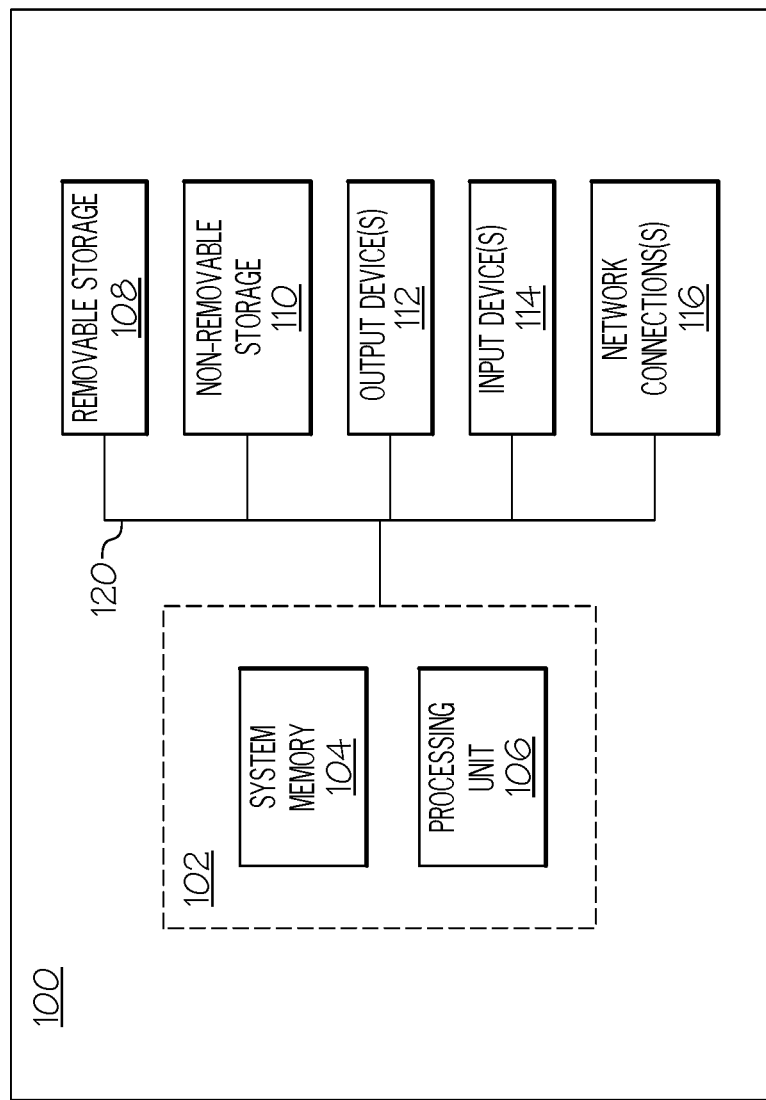

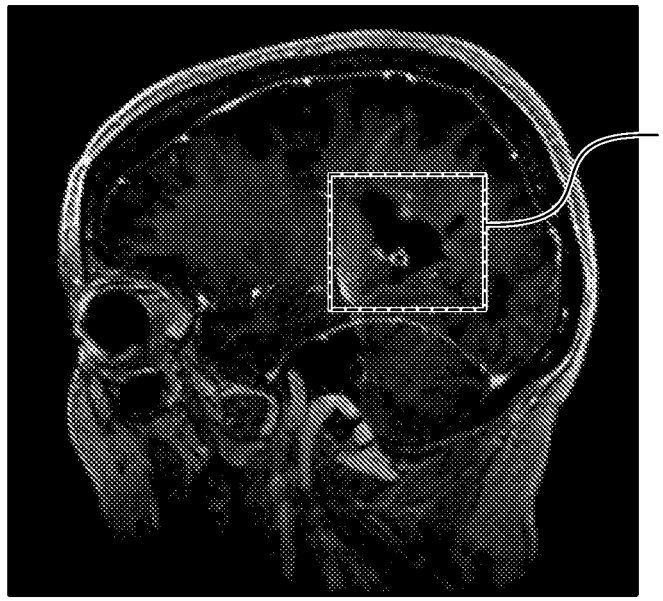
FIG. 3A
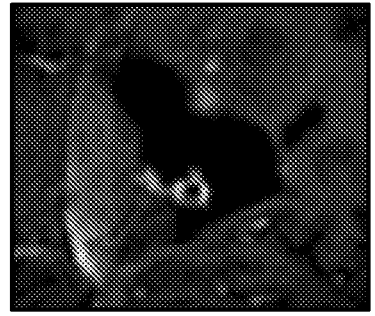
FIG. 3A1
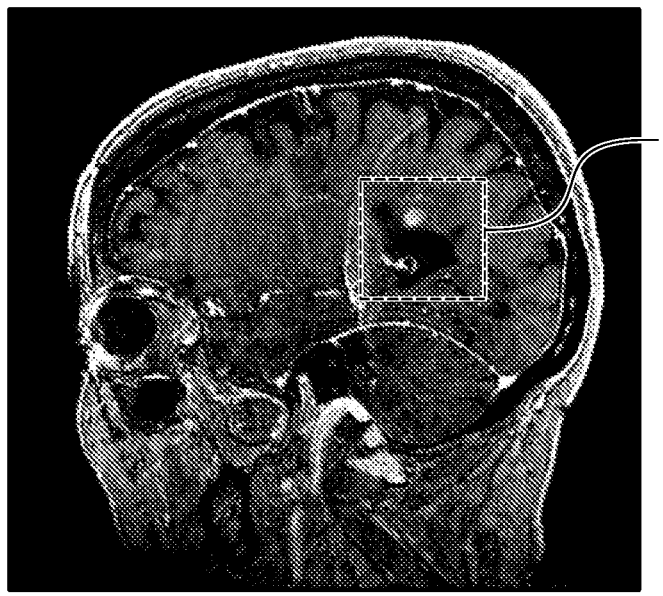
FIG. 3B
FIG. 3B1

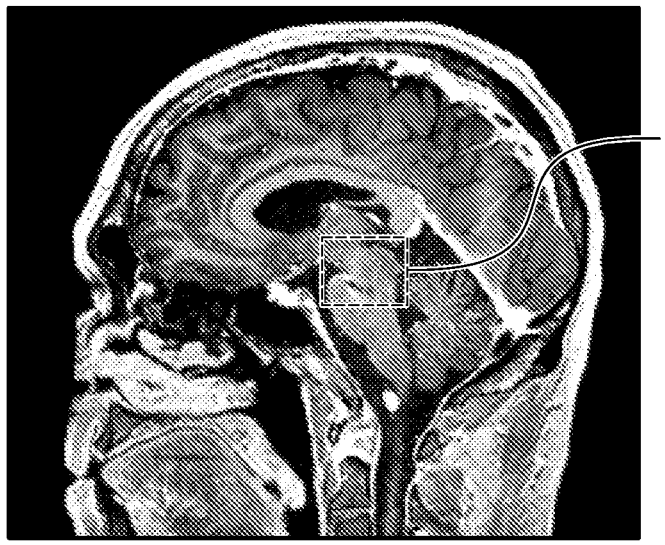
FIG. 4A
FIG. 4A1
FIG. 4B
FIG. 4B1

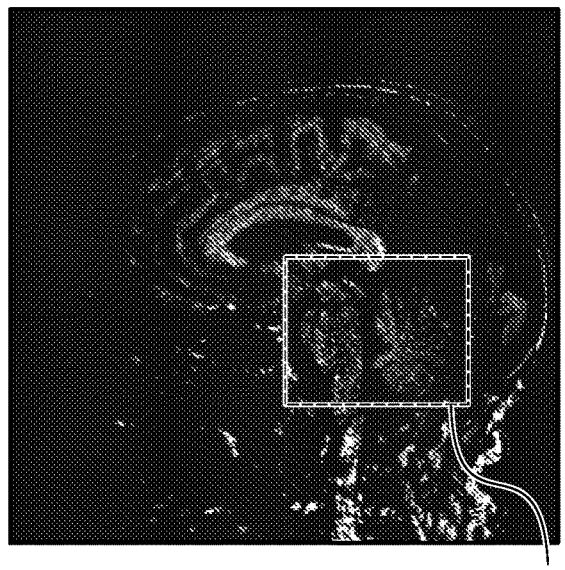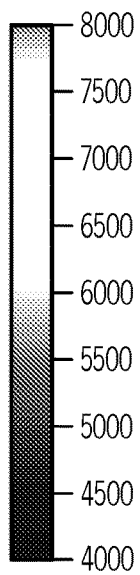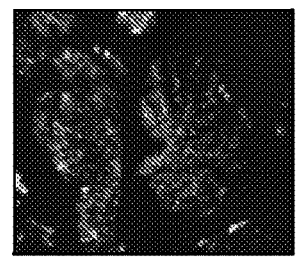
FIG. 6A  6A1
FIG. 6A1
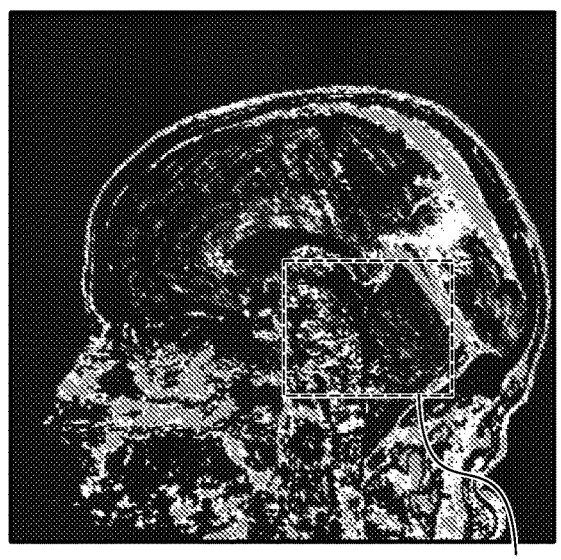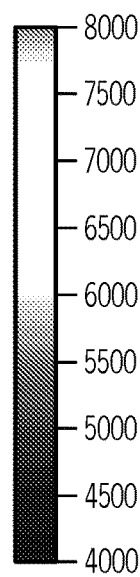
FIG. 6B  6B1
FIG. 6B1

SYSTEM AND METHOD FOR DETECTING SMALL BLOOD-TISSUE BARRIER DISRUPTION

CROSS-REFERENCE TO RELATED APPLICATION

This application is a national phase of International Application No. PCT/US2019/016954 filed on Feb. 7, 2019, which claims priority to U.S. Provisional Application No. 62/627,369 filed on Feb. 7, 2018, the entire contents of which is incorporated by reference.

BACKGROUND

Field of the Invention

The present invention relates to system and method for detecting small blood-tissue barrier breakdown using high-resolution contrast enhanced magnetic resonance imaging.

Description of the Related Art

Resonance Imaging (MRI) is one of the most important modern medical imaging modalities. It has far less risk of side effects than most other imaging modalities, such as radioscopy with x-rays or computed tomography, because patients and medical personnel are not subjected to ionizing radiation exposure in the procedure. The use of MRI has grown very fast. Every year, more than 30 million MRI scans are performed in the United States; more than 60 million MRI scans are performed worldwide. Doctors often recommend MRI for the diagnosis of various diseases, such as tumors, strokes, heart problems, and spine diseases. A high-quality scan is important for maximizing diagnostic sensitivity and accuracy. Generally, high quality images are characterized by high signal-to-noise ratio (SNR), high contrast between normal and pathological tissues, low levels of artifacts, and appropriate spatial-temporal resolution.

In order to obtain a detectable MR signal, the object/subject examined is positioned in a homogeneous static magnetic field, so that the object's nuclear spins generate net magnetization oriented along the static magnetic field. The net magnetization is rotated away from the static magnetic field using a radio frequency (RF) excitation field with the same frequency as the Larmor frequency of the nucleus. The angle of rotation is determined by the field strength of the RF excitation pulse and its duration. In the end of the RF excitation pulse, the nuclei, in relaxing to their normal spin conditions, generate a decaying signal (the "MR signal") at the same radio frequency as the RF excitation. The MR signal is picked up by a receive coil, amplified and processed. The acquired measurements, which are collected in the spatial frequency domain, are digitized and stored as complex numerical values in a "k-space" matrix. An associated MR image can be reconstructed from the k-space data, for example, by an inverse 2D or 3D fast Fourier transformation (FFT) from the raw k-space data.

Blood-tissue barrier (BTB) includes at least one of blood-brain barrier (BBB), but not limited to, blood-cerebrospinal fluid (CSF) barrier, the blood-retinal barrier, the blood-testis barrier. One of its major functions is to separate vital organs from external cues and harmful substances in the environment. These barriers safeguard key physiological processes in tissue corresponding organ. Understanding blood-tissue barriers has significance due to the difficulties faced by clinicians in early detection and treating various diseases. For example, the BBB disruption is not only being shown in numerous brain diseases, but animal studies have indicated that it plays a direct key role in the genesis of neurovascular dysfunction and associated neurodegeneration. BBB breakdown has been used as a significant marker for a wide variety of diseases such as brain tumors, Parkinson's disease, traumatic brain injury, vascular cognitive impairment, multiple sclerosis, stroke, chronic vascular disease, and in disorders with a primary neurodegenerative component such as Alzheimer's disease and dementia. BBB disruption is also a common pathological finding in many psychiatric disorders including schizophrenia, autism spectrum disorder (ASD) and mood disorders. Moreover, the severity of various diseases is proportional to the degree of BBB disruption. The subtle disruption of the BBB provides a measure of that various diseases at the early stage. Interest in the role of the BBB has surged in the past 10 years as an increasing number of neurological diseases have been linked to BBB disruption. There remains an unmet need to develop novel method to estimating subtle change of BBB disruption.

Measuring BBB permeability in humans is not straightforward. The cerebrospinal fluid/serum albumin ratio is a common and well-established method to assess BBB permeability, but it is invasive and there are concerns that it does not reliably reflect BBB permeability. Medical imaging after an intravenous injection of tracer is an attractive technique to measure BBB permeability. The basic principle of estimating BTB is identical for all imaging modalities. BTB breakdown or disruption of pathological tissue is estimated by measuring a tracer or contrast agent, which does not cross BTB under normal physiological conditions. The tracers used for estimating BTB are either exogenous tracers or endogenous tracers. Many image modalities are available to quantitatively measure BTB breakdown or disruption, including computed tomography (CT), single photo-emitting computed tomography (SPECT) and MRI. The use of SPECT is limited because of the low spatial resolution, less sensitive for small BTB lesions and ionizing radiation. The advantages of using dynamic contrast enhanced-CT (DCE-CT) include short exam time and better availability than MRI in clinical settings. However, its applications are limited by some disadvantages, including ionizing radiation, bad soft tissue contrast and an increasing risk for adverse reactions caused by iodinated contrast agent. Currently, dynamic contrast agent MRI, a $T_1$-weighted acquisition dynamic contrast-enhanced magnetic resonance imagining (DCE-MRI), and a $T_2^*$-weighted acquisition dynamic susceptibility contrast (DSC-MRI), can be used to measure BTB permeability which has some advantages, including no ionizing radiation, and good soft tissue contrast. Although DCE-MRI has been shown to be a robust research tool, it does not become part of standard clinical practice yet. This is partly due to some of the limitations of DCE-MRI, including expensive procedure, multicompartment physiologic models, complex data analysis methods and long exam time. Dynamic susceptibility contrast magnetic resonance imaging (DSC-MRI) is also used to estimate BBB disruption. Because the bolus transit time for DSC-MRI imaging is so short, a fast acquisition technique provides the necessary temporal resolution to adequately characterize the transient drop in signal intensity. DSC-MRI is also limited by susceptibility artifacts and contrast leakage. The major challenge for both DCE-MRI and DSC-MRI is low spatial resolution which is caused by the high temporal resolution for dynamic contrast MRI techniques. In most case, one must trade-off total scan time, spatial-temporal resolution and detection sensitivity when these two sequences are used to estimate BBB disruption. Currently, the spatial resolution for DCE-MRI and DSC-MRI is less than 8 mm$^3$ for a voxel and 4 mm$^2$ for a pixel in clinical practice. Some previous study indicated that low BBB leakage rates are associated with the early stage of the diseases. Currently, dynamic contrast MRI techniques are one of the most sensitive methods to clinically detect early changes in BBB permeability. But the reliable measurement of low-level BBB permeability remains a difficult problem by dynamic contrast MRI. In order to obtain precise results about BBB disruption, the longer scan time is required. It also implies that the accumulation of the BBB disruption influenced the detection sensitivity.

U.S. Patent Application Publication No. 2012/0179028A1 to Peter Caravan et al. discloses a method to measure a permeability of a subject's blood-brain barrier to water by the two $T_1$ maps acquired at the different time frames before and after administration of a contrast agent.

U.S. Pat. No. 9,599,625 B2 to Liu et al discloses methods and apparatus for determining BBB damage due to an ischemic event through detecting the presence of occluding fragments in a blood sample.

U.S. Pat. No. 9,194,867 B2 to Aristo Vojdani discloses methods, assays, and apparatus for testing of antigens (such as blood, saliva or other bodily fluid) associated with intestinal and/or BBB permeability.

U.S. Patent Application Publication No. 2015/0141804 A1 to William Rooney et al. discloses methods and apparatuses for determining a level of cellular metabolic activity for a region of interest in order to detect and map on-going gliovascular unit metabolic activity using high-resolution MRI. They focus on dynamic contrast enhanced MRI (DCE-MRI) time-course data for estimating metabolic activity.

U.S. Patent Application Publication No. 2015/0265210 A1 to David Israeli et al. discloses a method of analyzing a blood-brain barrier of a subject having a detectable dose of an MRI contrast agent by comparing two or more of the magnetic resonance images so as to determine variations in concentration of the contrast agent in the organ. Their images are acquired with relatively low resolution (voxel size of about 2 or 4 mm$^3$).

U.S. Pat. No. 9,046,589 B2 to Kjell-Inge Gjesdal et al. discloses methods, apparatus, and computer based systems for identifying benign and malignant tumors in tissues such as soft tissues and particularly breast tissue using DCE-MRI and dynamic susceptibility contrast-enhanced magnetic resonance imagining (DSC-MRI) of the tumors. This success for both methods is due to the methods ability to identify physiological differences in cancer tissue through the quantifying of the contrast agent in the tissue over time.

U.S. Patent Application Publication No. 2014/0086827 A1 to Damir Janigro et al. discloses a method of assessing blood brain barrier permeability through S 100BB homodimer.

International Publication No. WO 2014/205338A3 and U.S. Patent Application Publication No. 2016/0120893A1 to Chenghua Gu and Ayal Ben-Zvi disclose a method to modulate the permeability of the blood-brain barrier for therapeutic purposes.

U.S. Pat. No. 9,291,692 B2 to Feng-Yi Yang et al. discloses a method of assessing the blood-brain barrier recovery curve using a focused ultrasound DCE-MRI technique.

International Publication No. WO 2016/042554A1 and U.S. Patent Application Publication No. 2017/0247429A to Itzik Cooper et al. discloses a method to develop novel BBB penetrating agents for the treatment of brain diseases and disorders.

International Publication No. WO 2015/138974A1 and U.S. Pat. No. 9,913,899 B2 to Lawrence M. Kauvar and Damir Janigro discloses a method to test the blood of a patient for total S-100B or for S-100BB as a marker of blood brain barrier integrity to reduce neuronal damage caused by a cerebral ischemic event in a human patient.

International Publication No. WO 2017/021951A1 to Alon Friedman and Yehuda Vazana discloses a method for reducing the permeability of the blood-brain-barrier in a patient by administration of a composition which includes N-methyl-d-aspartate receptor antagonists.

International Publication No. WO 2017/048778A1 and U.S. Patent Application Publication No. 2018/0256756A1 to Richard D. Kopke and Rheal A. Towner disclose a method to transport a therapeutic or diagnostic agent across a blood-brain barrier or a blood-cochlear barrier or a blood-cerebrospinal fluid barrier of a subject by administration of 2,4-disulfonyl a-phenyl tertiary butyl nitrone.

International Publication No. WO 2017/049411A1 and U.S. Patent Application Publication No. 2018/0250361A1 to Philippe Patrick Monnier et al. disclose a method to modulate the permeability of the blood brain barrier for the treatment of diseases, and promote re-myelination as well as prevent de-myelination.

U.S. Pat. No. 10,076,263B2 to Richard Leigh and Peter B. Barker discloses a method to estimate blood brain permeability imaging using dynamic susceptibility contrast magnetic resonance imaging.

This background information is provided for the purpose of making known information believed by the applicant to be of possible relevance to the present invention. No admission is necessarily intended, nor should be construed, that any of the preceding information constitutes prior art against the present invention.

SUMMARY

This disclosure describes method and system to detect small blood-tissue barrier breakdown using contrast enhanced magnetic resonance imaging (CE-MRI) herein. It should be understood that this disclosure contemplates using positive contrast agents other than Gd-based contrast agents, which are provided as an example only, with the techniques described herein. As a result, this disclosure makes contrast enhanced MRI safer, faster, and more effective for all research, drug development and medical applications.

In one embodiment, a method for detecting blood-tissue barrier breakdown or disruption is provided. The method includes acquiring first image data of a target region of a subject with a predetermined spatial resolution; administrating exogenous or endogenous tracer into the subject; acquiring at least one image data of the target region with the predetermined spatial resolution after administration of the tracer; differentiating healthy tissue and pathological tissue with blood-tissue barrier breakdown in the target region based on entire of part of the acquired first image data and the acquired at least one image data; and visualizing or analyzing the blood-tissue barrier breakdown of pathological tissue based on the differentiation.

In another embodiment, a system for detecting blood-tissue barrier breakdown or disruption is provided. The system includes a receiver configured to acquire image data of a target region of a subject with a predetermined spatial resolution; and a processor configured to: receive, from the receiver, first image data of the target region of the subject before an exogenous or endogenous tracer is administered to the subject; receive, from the receiver, at least one image data of the target region of the subject after the exogenous or endogenous tracer is administered into the subject; differentiate pathological tissue with blood-tissue barrier breakdown from healthy tissue in the target region based on entire of part of the acquired first image data and the acquired at least one image data; and visualize or analyze the blood-tissue barrier breakdown of the pathological tissue based on the differentiation.

Alternatively or additionally, in some implementations, the detectable small blood-tissue barrier breakdown of pathological tissue can be further implemented for early detection of various diseases, including tumor, multiple sclerosis, Parkinson's disease, vascular cognitive impairment, chronic vascular disease but not limited to, inflammation disease, infection disease, stroke, traumatic nerve injury, vascular disease, Alzheimer's disease, dementia, schizophrenia, autism spectrum disorder and mood disorders.

Alternatively or additionally, blood-tissue barrier is detected by at least one of, a magnetic resonance imaging (MRI) apparatus, a positron emission tomography (PET) apparatus, a computed tomography (CT) apparatus, and a single positron emission computed tomography (SPECT) apparatus.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 1A is an example computing device.

FIG. 3A depicts a brain image of a patient with MS by a conventional routine protocol, at the voxel spatial resolution of 1 mm$^3$ at 3.0 Tesla.

FIG. 3A1 depicts an enlarged view of a portion indicated as 3A1 in FIG. 3A.

FIG. 3B depicts a brain image of a patient with MS according to the optimal protocol of the present disclosure at the voxel spatial resolution of 0.34 mm$^3$ at 3.0 Tesla.

FIG. 3B1 depicts an enlarged view of a portion indicated as 3B1 in FIG. 3B.

FIG. 4A shows an example of detecting blood-tissue barrier breakdown of a patient with brain tumor at the voxel spatial resolution of 1 mm$^3$ at 3.0 Tesla.

FIG. 4A1 depicts an enlarged view of a portion indicated as 4A1 in FIG. 4A.

FIG. 4B shows an example of detecting blood-tissue barrier breakdown of a patient with brain tumor at the voxel spatial resolution of 0.34 mm$^3$ at 3.0 Tesla.

FIG. 4B1 depicts an enlarged view of a portion indicated as 4B1 in FIG. 4B.

FIG. 5A1 depicts an enlarged view of a portion indicated as 5A1 in FIG. 5A.

FIG. 5B1 depicts an enlarged view of a portion indicated as 5B1 in FIG. 5B.

FIG. 6A shows an example of detecting blood-tissue barrier breakdown of a patient with Parkinson's disease at the voxel spatial resolution of 0.512 mm$^3$ before contrast agent is administrated.

FIG. 6A1 depicts an enlarged view of a portion indicated as 6A1 in FIG. 6A.

FIG. 6B shows an example of detecting blood-tissue barrier breakdown of a patient with Parkinson's disease at the voxel spatial resolution of 0.512 mm$^3$ after contrast agent is administrated.

FIG. 6B1 depicts an enlarged view of a portion indicated as 6B1 in FIG. 6B.

DETAILED DESCRIPTION

Figure 1:
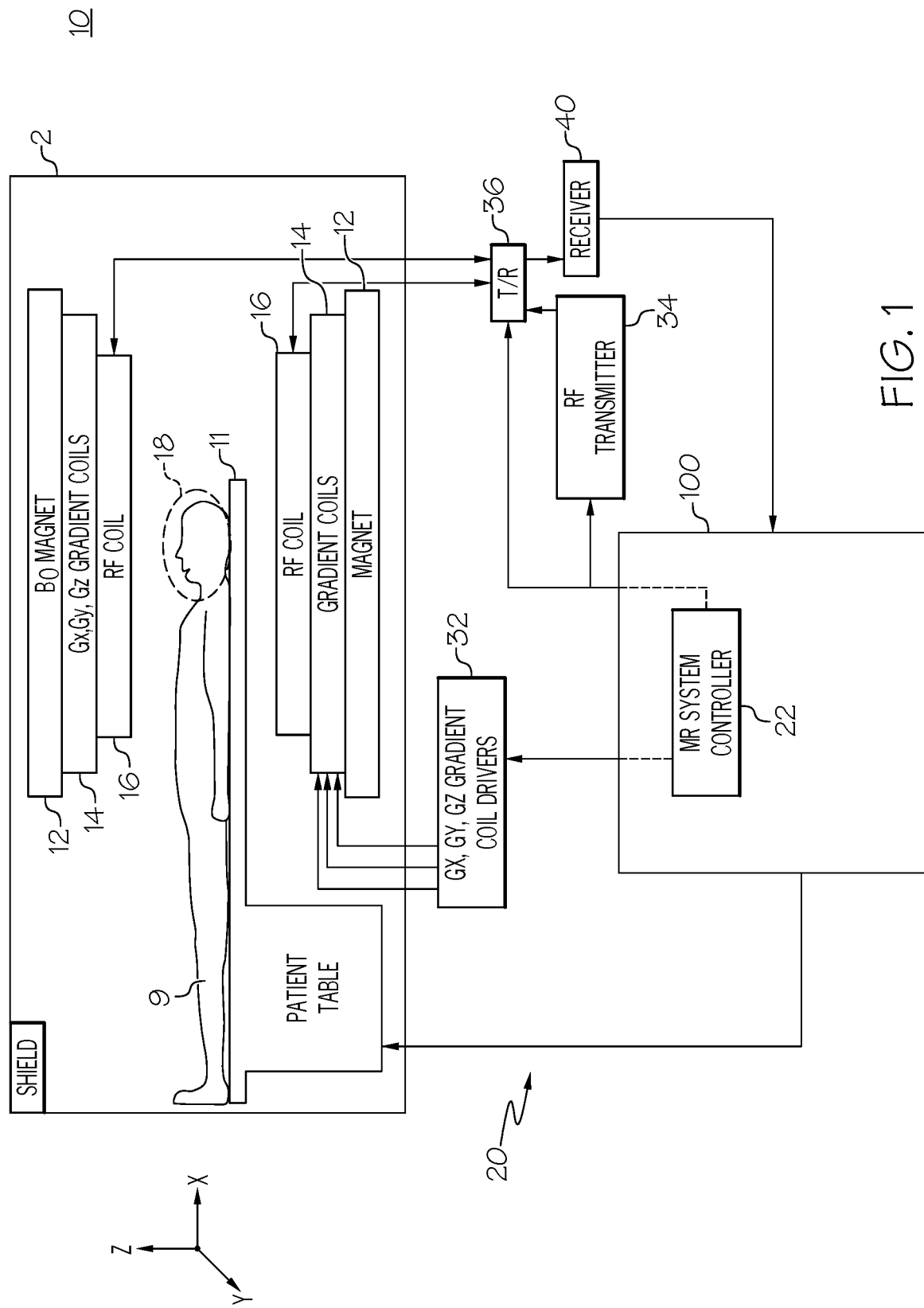
FIG. 1 is a diagram illustrating an example MRI system.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not.

The term "exogenous tracer" as used herein is a substance used to increase the contrast or improve more information of structures or fluids within the body in medical imaging. The exogenous tracer may be used to diagnose disease as well as monitor treatment effects. The exogenous tracer may be administered by oral or intravenous administration. For example, MRI contrast agents are used to improve the visibility of internal body structures. The most commonly used compounds for contrast enhancement are gadolinium-based compounds which shorten the relaxation times following oral or intravenous administration. The disadvantage of exogenous tracers is that there are side effects associated with the administration of the tracers. For example, the injection of exogenous agent of Gd-based contrast agent in MRI has potential side effects of nephrogenic systemic fibrosis (NSF), deposition of Gd molecules, and potential neurotoxicity.

The term "endogenous tracer" as used herein does not use external exogenous tracers, but instead depend on the intrinsic ability to increase the contrast or improve more information of structures or fluids within the body in medical imaging. For example, arterial spin labelling MRI uses magnetically labeled arterial blood water protons as an endogenous tracer to measure tissue perfusion. The endogenous tracer method has a very promising clinical screening and management because the injection of exogenous agent has potential risk for patients.

The term "blood tissue barrier" as used herein includes at least one of blood-brain barrier, but not limit to, blood-cerebrospinal fluid (CSF) barrier, the blood-retinal barrier, the blood-testis barrier.

The term "blood brain barrier (BBB)" as used herein is a highly selective border that separates the circulating blood from the brain. The blood-brain barrier is composed of endothelial cells of the capillary wall, astrocyte end-feet ensheathing the capillary, and pericytes embedded in the capillary basement membrane. BBB greatly restrict exchange of substances between capillaries and brain tissue.

The term "blood-CSF barrier" as used herein is an obstruction or a partition separating the blood from CSF.

The term "blood-retinal barrier" consists of cells that are joined tightly together to prevent certain substances from entering the tissue of the retina. Diabetic retinopathy is related to the breakdown of the blood-retinal barrier The terms "therapy" and "treatment" as used interchangeably herein, refer to an intervention performed with the intention of improving a subject's status.

The terms "detection" and "diagnosis" as used interchangeably herein, refer to identify the abnormal tissue or lesion.

MRI System Overview

FIG. 1 depicts an MRI system 10, according to one or more embodiments described and shown herewith. In embodiments, the MRI system 10 shown in FIG. 1 includes a patient table 11, a static magnetic field generating unit 12, a gradient magnetic field generating unit 14 for generating respective magnetic fields in proximity to a target area 18 of an object 9, a transmitting and receiving unit 16, and a computing device 100. The patient table 11, the static magnetic field generating unit 12, the gradient magnetic field generating unit 14, and the transmitting and receiving unit 16 are placed within MRI RF shielding area 2 where noise of radio frequency is prevented from entering.

The static magnetic field generating unit 12 includes a main magnet configured to generate a strong static magnetic field in proximity to the target area 18 of the object 9. The static magnetic field generating unit 12 may be arranged to surround the target area 18 of the object 9. For example, the static magnetic field generating unit 12 may be a cylindrical-shaped unit. The gradient magnetic field generating unit 14 includes gradient magnetic field coils for generating gradient magnetic fields in an x-axis direction, a y-axis direction, and a z-axis direction, which are orthogonal to each other. The gradient magnetic field generating unit 14 may be arranged to surround the target area 18 of the object 9. For example, the gradient magnetic field generating unit 14 may be a cylindrical-shaped unit.

In embodiments, the transmitting and receiving unit 16 may include a transmission coil and a receiving coil. The transmission coil irradiates RF pulses to the object 9 and the receiving coil receives MR signals generated by the object 9. In some embodiments, the transmitting and receiving unit 16 may include a transceiver coil having the functions of both the transmission coil and the receiving coil. The receiving coil may be composed of, for example, a so-called array coil in which, for example, a plurality of coil elements are disposed to detect the MR signals generated by the object 9. An RF transmitter 34 may control the transmission coil of the transmitting and receiving unit 16 to irradiate RF pulses. A receiver 40 may receive MR signals generated by the object 9 from the receiving coil of the transmission and receiving unit 16. The RF transmitter 34 and the receiver 40 may communicate with the transmitting and receiving unit 16 through a transmitter/receiver interface 36.

In embodiments, the MRI system 10 includes the computing device 100. The computing device 100 includes a MRI system controller 22. The MRI system controller 22 may control the operations of the gradient coil drivers 32 that activate the gradient coils of the gradient magnetic field generating unit 14. The MRI system controller 22 may also control the operations of the RF transmitter 34 that activates the RF coil of the static magnetic field generating unit 12. The computing device 100 may receive MR signals from the receiving coil of the transmission and receiving unit 16 and reconstruct an MRI image based on the received MR signals. The details of the computing device 100 will be further described with reference to FIG. 1A below.

In embodiment, the computing device 100 may be operably coupled to other components of the MRI system 10, for example, using by any medium that facilitates data exchange between the components of the MRI system 10 and the computing device 100 including, but not limited to, wired, wireless and optical links. For example, the computing device 100 may convert the MR signals received from the transmitting and receiving unit 16 into k-space data. The computing device 100 may generate MR image data from the k-space data with image reconstruction processing. In some embodiments, the techniques for improving image quality with optimal variable flip angles may optionally be implemented using the MRI system 10.

Example Computing Device

FIG. 1A depicts a computing device 100 according to one or more embodiments shown and described herein. It should be appreciated that the logical operations described herein with respect to the various figures may be implemented (1) as a sequence of computer implemented acts or program modules (i.e., software) running on a computing device (e.g., the computing device described in FIG. 1A), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

It should be understood that the computing device 100 is only one example of a suitable computing environment upon which embodiments of the invention may be implemented. Optionally, the computing device 100 may be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In embodiments, the computing device 100 includes a controller 102 that includes one or more processing units 106 and one or more system memory modules 104. The controller 102 may be the same controller as the MRI system controller 22 in FIG. 1. In other embodiments, the controller 102 may be a separate controller from the MRI system controller 22 in FIG. 1. Depending on the exact configuration and type of computing device, the one or more memory modules 104 may be volatile (such as random access memory (RAM)), non-volatile (such as read-only memory (ROM), flash memory, etc.), or some combination of the two. The one or more processing units 106 may be a standard programmable processor that performs arithmetic and logic operations necessary for operation of the computing device 100.

In embodiments, the computing device 100 includes communication path 120 that provides signal interconnectivity between various components of the computing device 100. Accordingly, the communication path 120 may communicatively couple any number of processing units 106 with one another, and allow the components coupled to the communication path 120 to operate in a distributed computing environment. Specifically, each of the components may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

Accordingly, the communication path 120 may be formed from any medium that is capable of transmitting a signal such as, for example, conductive wires, conductive traces, optical waveguides, or the like. In some embodiments, the communication path 120 may facilitate the transmission of wireless signals, such as Wi-Fi, Bluetooth, Near Field Communication (NFC) and the like. Moreover, the communication path 120 may be formed from a combination of mediums capable of transmitting signals. In one embodiment, the communication path 120 comprises a combination of conductive traces, conductive wires, connectors, and buses that cooperate to permit the transmission of electrical data signals to components such as processors, memories, sensors, input devices, output devices, and communication devices. Accordingly, the communication path 120 may comprise a vehicle bus, such as for example a LIN bus, a CAN bus, a VAN bus, and the like. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium.

The one or more processing units 106 may be configured to execute program code encoded in tangible, computer-readable media. Tangible, computer-readable media refers to any media that is capable of providing data that causes the computing device 100 (i.e., a machine) to operate in a particular fashion. Various computer-readable media may be utilized to provide instructions to the one or more processing units 106 for execution. Example tangible, computer-readable media may include, but is not limited to, volatile media, non-volatile media, removable media and non-removable media implemented in any method or technology for storage of information such as computer readable instructions, data structures, program modules or other data. One or more system memory modules 104, a removable storage 108, and a non-removable storage 110 are all examples of tangible, computer storage media. Tangible, computer-readable recording media may include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In embodiments, the one or more processing units 106 may execute program code stored in the one or more system memory modules 104. For example, a bus may carry data to the one or more system memory modules 104, from which the one or more processing units 106 receive and execute instructions. The data received by the one or more system memory modules 104 may be optionally stored on the removable storage 108 or the non-removable storage 110 before or after execution by the processing unit 106.

In embodiments, the computing device 100 may include additional storage such as removable storage 108 and non-removable storage 110 including, but not limited to, magnetic or optical disks or tapes.

The computing device 100 may also have input device(s) 114 such as a keyboard, mouse, touch screen, etc. The input device may be manipulated by an operator to input signals to the MRI apparatus to set the imaging method group, the performing order, the imaging condition, and the like. The computing device 100 may also have output device(s) 112 such as a display, speakers, printer, etc. The output device 112 may output image data such as local image data, diagnosis image data using display, printer and other displayer. The additional devices may be connected to the bus in order to facilitate communication of data among the components of the computing device 100.

Computing device 100 may also contain network connection(s) 116 that allow the device to communicate with other devices. The network connection(s) 116 may be any device capable of transmitting and/or receiving data via a wireless network. Accordingly, the network connection(s) 116 may include a communication transceiver for sending and/or receiving data according to any wireless communication standard. For example, the network connection(s) 116 may include a chipset (e.g., antenna, processors, machine readable instructions, etc.) to communicate over wireless computer networks such as, for example, wireless fidelity (Wi-Fi), WiMax, Bluetooth, IrDA, Wireless USB, Z-Wave, ZigBee, or the like.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

In some embodiments, the computing device 100 may include a workflow setting unit, an imaging operation determining unit, and an image reconstruction unit. The workflow setting unit may be a program module stored in the system memory modules 104. The workflow setting unit sets a first workflow relating to the MRI examination by estimating an imaging time of each of the imaging methods in the performing order initially set by a scan plan. Further, the workflow setting unit sets a second workflow relating to the MRI examination by estimating a shortest performing order, by which an examination time necessary to sequentially perform a plurality of imaging methods constituting the imaging method group set by the input unit is minimized. The imaging operation determining unit determines whether an imaging operation during a main imaging is implemented according to the workflow. In embodiments, the workflow setting unit and/or the imaging operation unit may be implemented using hardware, software, and or a combination thereof.

The image reconstruction unit may include an MR signal storage unit, a signal processing unit, and an image data storage unit. The MR signal storage unit (e.g., memory) stores the MR signals, which are collected by the receiver unit of the transmitting and receiving unit 16. The signal processing unit has an image reconstruction processing unit and an image processing unit. The image reconstruction processing unit generates image data from the MR signal storage unit by image reconstruction processing, for example, performed by a Fourier transformation such as 2D FFT. When the MR signals to a three-dimensional region are collected, the image reconstruction processing unit of the signal processing unit generates volume data. Subsequently, the image processing unit generates three-dimensional image data such as volume rendering image data, surface rendering image data and the like or two-dimensional image data, multi planar reconstruction image data, and the like, because predetermined image processing is performed for the volume data generated by the image reconstruction processing unit. Then, the image data described above obtained by the signal processing unit are stored to the respective storage regions of the image data storage unit.

Lesion Detection Theory
(1) Image Quality Metric

SNR is used in imaging as a physical measure of the sensitivity of an imaging system which is defined as:

$$SNR = \mu_{signal}/\sigma_{background} \quad \text{Equation (1)}$$

where $\mu_{signal}$ is the average signal intensity of region of interest (ROI). $\sigma_{background}$ is the standard deviation of signal intensity of background region. The SNR efficiency, $SNR_{eff}$, is used to quantitatively evaluate image quality and efficiency. It is defined as SNR per square root total scan time (TA), is given by Equation (2) below.

$$SNR_{eff} = SNR/\sqrt{TA} \quad \text{Equation (2)}$$

A single type of tissue may have different signal intensities because of signal inhomogeneity caused by non-uniform transmit field and receive sensitivity. Thus, SNR of the single tissue may not be the best metric to evaluate image quality sometimes. Instead, global SNR may be used as an indicator to evaluate the image quality, avoiding the error caused by signal inhomogeneity.

As used herein, contrast is defined as:

$$\text{Contrast} = \mu_A - \mu_B, \quad \text{Equation (3)}$$

where $\mu_A$ and $\mu_B$ are the average signal value of regions A and B, respectively. It should be understood that other definitions of contrast may also be used as the objective function, such as Weber contrast and Michelson contrast, for example.

CNR is used as a metric to determine image quality, and is defined as:

$$CNR = \text{Contrast}/\sigma_{background} \quad \text{Equation (4)}$$

The CNR efficiency is defined as CNR per square root of total scan time (TA) as given by Equation (5) below:

$$CNR_{eff} = CNR/\sqrt{TA}; \quad \text{Equation (5)}$$

The enhancement of lesion (EL) (also referred to herein as a lesion enhancement metric) is used to describe the change in signal intensity of a lesion (also referred to herein as lesion tissue) in images acquired before and after the administration of contrast agent, respectively. The lesion enhancement metric is MR signal change before and after the administration of contrast agent, that is, the lesion enhancement metric (EL) is defined by Equation (6) below:

$$EL = \frac{S_a - S_b}{S_b}; \quad \text{Equation (6)}$$

where $S_a$ is signal intensity of a contrast enhanced lesion region of interest (ROI) caused by BTB breakdown or disruption after the administration of contrast agent, and $S_b$ is signal intensity of lesion tissue without contrast administration or healthy tissue, respectively.

Generally, detection sensitivity for BTB breakdown or disruption is determined by the method used for detecting BTB breakdown or disruption. For example, detection sensitivity may be estimated by the contrast or contrast variations between tissue with BTB breakdown or disruption and healthy tissue around it or the contrast or contrast variations between tissue with BTB breakdown or disruption and tissue without BTB breakdown or disruption. To simplify the problem herein, the MRI properties of healthy tissue may be presumed to be the same as those of tissue without BTB breakdown. Thus, the detection sensitivity will be given by $$\text{detection sensitivity} \propto \text{contrast} = S_a - S_b \quad \text{Equation (7)}$$

Additionally, the spatial resolution of current MRI technique (around 1 millimeter) is always much greater than the size of pathological or healthy tissue cell (around tens micrometers). In a voxel or a pixel of an MRI image, pathological tissue cells mix with healthy tissue cells. The fraction of pathological tissue cells may be $\alpha$, and then the fraction of healthy tissue cells may be $1-\alpha$. From Equations (6) and (7), thus the detection sensitivity is simplified to:

$$\text{contrast} = \alpha \cdot EL \cdot S_b \quad \text{Equation (8)}$$

Generally, both MRI signal and contrast are proportional to the voxel size or pixel size for pure tissues or non-mixture tissue in different voxels or pixels. Thus, in general, increasing spatial resolution of MRI decreases the size of a voxel or a pixel for pure tissues or non-mixture tissue, and thus reduces MRI signal, and then contrast. Though Equation (8) are derived from contrast enhancement MRI, the theory is available for contrast enhanced MRI, DCE-MRI, DSC-MRI, Arterial spin labeling (ASL) MRI, intravoxel incoherent motion (IVIM) MRI for detecting BTB breakdown and disruption.

However, when a voxel or a pixel includes both healthy tissue cells and pathological tissue cells, the contrast depends on not only the voxel size or the pixel size, but also the fraction of pathological tissue cells as shown in Equation (8). In Equation (8), the contrast is proportional to the fraction of the pathological tissue cells. Thus, when the size of a voxel or a pixel decreases as spatial resolution increases, the fraction of pathological tissue cells a may increase. Thus, contrary to the conventional notion that contrast decreases as spatial resolution increases, the contrast may increase as the spatial resolution increases with respect to a voxel or a pixel having a mixture of healthy tissue cells and pathological tissue cells. Thus, the present disclosure obtains images with greater contrast for regions having a mixture of healthy tissue cells and pathological tissue cells by increase spatial resolution. Accordingly, the detection sensitivity of BTB breakdown increases as the predetermined spatial-resolution increases.

The increase of the spatial resolution may be limited by signal-to-noise ratio of the image. Various techniques, such as better coil design, high field strength and optimization of sequence, may improve the signal-to-noise ratio and lead to increased spatial resolution. For example, application of hybrid k-space trajectory and variable flip angle may improve the signal-to-noise ratio.

In embodiments, the spatial resolution of the MRI system may be set to be less than 3.4 mm$^3$ for a voxel of an image or 2.3 mm$^2$ for a pixel of the image. In another embodiment, the predetermined spatial resolution may be less than 1 mm$^3$ for a voxel of the image data or 1 mm$^2$ for a pixel of the image data. In another embodiment, the predetermined spatial resolution may be less than 0.5 mm$^3$ for a voxel of the image data or 0.64 mm$^2$ for a pixel of the image data. In another embodiment, the predetermined spatial resolution may be less than 0.3 mm$^3$ for a voxel of the image data or 0.5 mm$^2$ for a pixel of the image data. In another embodiment, the predetermined spatial resolution may be less than 0.13 mm$^3$ for a voxel of the image data or 0.25 mm$^2$ for a pixel of the image data.

Method

Figure 2:
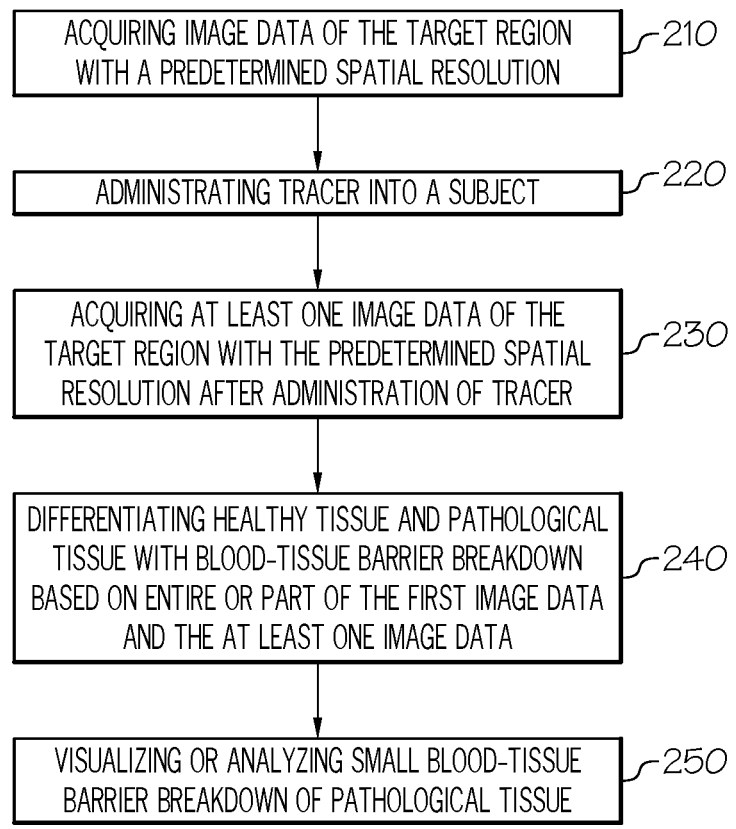
FIG. 2 is a flowchart illustrating example operations for detecting blood-tissue barrier breakdown using contrast agent magnetic resonance imaging.

FIG. 2 shows a flowchart illustrating example operations for detecting BBB breakdown using high resolution contrast agent MRI. The detection of BBB breakdown using high resolution contrast agent MRI can include the following steps.

In step 210, the MRI system 10 acquires image data of a target region with a predetermined spatial resolution. The predetermined spatial resolution may be less than 3.4 mm$^3$ for a voxel of an image or 2.3 mm$^2$ for a pixel of the image. In another embodiment, the predetermined spatial resolution may be less than 1 mm$^3$ for a voxel of the image data or 1 mm$^2$ for a pixel of the image data. In another embodiment, the predetermined spatial resolution may be less than 0.5 mm$^3$ for a voxel of the image data or 0.64 mm$^2$ for a pixel of the image data. In another embodiment, the predetermined spatial resolution may be less than 0.3 mm$^3$ for a voxel of the image data or 0.5 mm$^2$ for a pixel of the image data. In another embodiment, the predetermined spatial resolution may be less than 0.13 mm$^3$ for a voxel of the image data or 0.25 mm$^2$ for a pixel of the image data. The image data may be obtained a certain imaging sequence.

In step 220, exogenous or endogenous tracer is administered into a subject.

In step 230, the MRI system 10 acquires at least one image data of the target region with the predetermined spatial resolution after administration of the tracer.

In step 240, the MRI system 10 differentiates healthy tissue and pathological tissue with blood-tissue barrier breakdown in the target region based on the image data. In embodiments, Radiologists may visually differentiate healthy tissue. For example, only one MRI image may be acquired after the administration of an exogenous or endogenous tracer, and a radiologist may differentiate healthy tissue and pathological tissue with blood-tissue barrier breakdown in the target region based on the acquired image.

In some embodiments, image processing may be implemented on the acquired image data to identify very small BTB breakdown or disruption. When BTB breakdown or disruption is very small at the early of diseases, it is very difficult to detect the BTB breakdown or disruption visually. The computing device 100 may implement image processing on acquired images to increase the detection sensitivity of the pathological changes. For example, the computing device 100 may subtract the first image data from the image acquired after administration of contrast agent to visually detect the BTB changes or calculate the BTB permeability from several image data that were acquired after administrating exogenous or endogenous tracer.

In step 250, the MRI system 10 visualizes or analyzes the blood-tissue barrier breakdown of pathological tissue based on the differentiation. As described herein, the imaging sequence may include 2 dimensional or 3 dimensional, one slab or multiple slabs IR-GRE sequence, fast spin echo sequence, steady-state free precession sequence, but not limited thereto, and balanced steady-state free precession sequence with and/or without magnetization preparation.

This disclosure describes method and system to detect small blood-tissue barrier breakdown using high resolution contrast enhanced magnetic resonance imaging (CE-MRI) herein. It should be understood that the proposed method may be available for other image modalities to estimate blood-tissue barrier breakdown, such as a positron emission tomography (PET) apparatus, a computed tomography (CT) apparatus, and a single positron emission computed tomography (SPECT) apparatus. Additionally, it should be understood that this disclosure contemplates using positive contrast agents other than Gd-based contrast agents, which are provided as an example only, with the techniques described herein. As a result, this disclosure makes contrast enhanced MRI safer, faster, and more effective for all research, drug development and medical applications.

Alternatively or additionally, the exogenous tracer may be either positive contrast agent or negative contrast agent. The images are acquired with $T_1$-weighted MRI sequence for positive contrast agent, and $T_2^*$-weighted sequence for negative contrast agent. Alternatively or additionally, $T_1$-weighted magnetic resonance imaging comprises 2 dimensional or 3 dimensional $T_1$-weighted sequences with and without magnetization preparation. The magnetization preparation may be at least one of inversion recovery pulse, saturation pulse, but not limited to, and various background suppression pulses.

Alternatively or additionally, high spatial resolution may be determined by at least one of the target region size, signal-to-noise of normal tissue, contrast enhancement after the administration of contrast agent, a lesion enhancement, but not limited to, fraction of blood-tissue barrier breakdown in a voxel or pixel, total scan time, and contrast agent concentration. As described herein, a contrast enhancement is used to describe the change in contrast change between a lesion and around tissue in images after the administration of contrast agent.

Optionally, differentiating normal tissue and pathological tissue with blood-tissue barrier breakdown may be either quantitative or qualitative.

Optionally, the region of interest may include at least one of a lesion, a landmark, a texture, or a feature of interest.

Examples

BBB disruption is linked to various brain seizures, brain injury, BBB pathology, and psychiatric disorders. They include a neurodegenerative disease, such as multiple sclerosis, Parkinson's disease, Huntington's disease, Pick's disease, Alzheimer's disease, amyotrophic lateral sclerosis, dementia, and stroke, and peripheral neuropathy. They also include brain tumors and major depression, diabetes, and obesity. BBB disruption is also a common pathological finding in many psychiatric disorders including schizophrenia, autism spectrum disorder and mood disorders. Therefore, it would be desired to have a system and method for detecting changes in the BBB, including large and small changes in the permeability and the impermeability of the BBB. Since a variety of diseases are associated with subtle changes in the BBB at an earlier stage, it would be highly desirable to have clinically useful tools for readily assessing the subtle changes in the BBB in human subjects.

Currently, the most widely used method to evaluate BBB permeability is by using Gadolinium (Gd) contrast agent MRI to observe post-contrast $T_1$ enhancement qualitatively or measure dynamic contrast enhanced (DCE) MRI signal quantitatively. In the past decades, contrast agent MRI has been used in more than 100 million patients with a broad spectrum of central nervous system disorders with BBB breakdown, ranging from multiple sclerosis, stroke, and infection to brain tumors, for both detection and therapeutic guidance. In the brain, Peristyles in the wall of small blood vessels such as capillaries, pre-capillary arterioles, and post-capillary venules control key neurovascular functions, such as the BBB integrity and cerebral blood flow. Pericyte degeneration leads to BBB breakdown and impaired hemodynamic responses, resulting in small vessel disease, white matter disease and cognitive impairment such as Alzheimer's, and stroke. The increased BBB permeability/leakage was consider as a consequence of ongoing processes like inflammation, atherosclerosis, and lack of vaso-autoregulation or microthrombosis. Recently, clinical MRI studies indicate that BBB leakage could be a primary reason for the development of vascular/brain parenchymal injury during aging. Worldwide, neurodegenerative diseases account for more than 20 million patients. Aging greatly increases the risk of neurodegenerative disease while the average age is steadily increasing. According to the World Health Organization, the proportion of the world's population over 60 years is expected to double from 12 to 22% between 2015 and 2050. A large variation in the permeability values in brain tumor are easily detected by DCE-MRI. But BBB breakdown in neuro-inflammatory diseases at an early stage is difficult to detect in a high level of accuracy and precision because the permeability is low in the early stage of the neuro-inflammatory diseases (at least one to two orders of magnitude lower than those found in brain tumor).

Example No. 1. Alzheimer Disease (AD)

AD will impact~10 million in the US alone by 2050. Clinical diagnosis of AD is more accurate in later stages of the disease. Early stage AD is more difficult to diagnose. Clinical symptoms appear after significant deposition of AD has already occurred. The ability to detect early stage AD in a specific and sensitive manner prior to the occurrence of significant impairment, and the advent of new therapeutic agents that work by arresting Aβ accumulation or depletion of Aβ levels in the brain, are important to early treatment and inhibition of disease progression. Thus, a need exists for methods which diagnosis Alzheimer's disease before significant neuronal loss has occurred, and for therapeutic treatments to prevent progression of the disease.

Cortical atrophy, neuronal loss, region-specific amyloid deposition, neuritic plaques (NP), and neurofibrillary tangles (NFT) are key neuropathological features in the AD brain. Numerous neuropathological studies indicate that the degenerative process starts from hippocampal region of the brain. Preclinical diagnosis of AD is one of the major challenges for the prevention of AD. The use of FDG-PET and amyloid PET imaging not only reveal preclinical pathologic changes in the early stage of AD, but also monitor progression and therapeutics. PET exam relies on expensive machinery and procedures that are not available in many hospitals and PET is associated with concerns of radiation exposure. Additionally, hippocampus volumetric based on MRI is one of the most reliable biomarkers of AD for an established AD diagnosis and follow-up of disease progression. In early stages of AD, progression of NFT pathology in the medial temporal lobe and hippocampus is not uniform: this pathology displays in perirhinal cortex and then is followed by involvement of the entorhinal cortex and then cornu ammonis 1 (CA1) subfield of the hippocampus proper. Additionally, pathological validation revealed that that hippocampal subfields were associated with αβ, tau, and neuronal count. As such, more global measures of medial temporal lobe structure may obscure these more specific regional changes at early stages. Unfortunately, each hippocampal subfield is a very small volume, and the limited spatial resolution obtained by MR systems with magnetic fields lower than 3T does not allow detecting small volumetric differences and subtle changes within these structures. Most recently, measurement of hippocampal subfields in vivo has become feasible due to advances in MRI spatial resolution. Most recently, the study implement DCE-MRI to find patients with early Alzheimer disease have significantly more tissue characterized by global BBB leakage than do healthy control subjects. Additionally, DCE-MRI further indicate that loss of cerebrovascular integrity during normal aging and aging associated with MCI that begins in the hippocampus may contribute to early stages of dementia associated with AD. However, it is very difficult to measure the leakage of BBB for the patients with AD because the leakage is slow, resulting in very small signal changes—typically 5% or lower over 20 min.

Example No. 2 Multiple Sclerosis (MS)

MS is the most common demyelinating neurodegenerative disease of the central nervous system (CNS), affecting an estimated 400.000 people in the U.S. and 2 million people worldwide. It is the leading cause of neurological severe and irreversible clinical disability in young and middle-aged adults. MS causes both cognitive and physical disability that frequently leads to unemployment, and thus is a major health concern with considerable economic consequences. Over the last twenty years, tests such as MRI, examination of CSF, and evoked response testing have played an increasingly important role in the diagnostic process. In 2005, revised McDonald criteria for multiple sclerosis were published. The revised criteria provide specific guidelines for using findings of MRI, cerebrospinal fluid analysis and visual evoked potentials to support a diagnosis of multiple sclerosis. However, even with these revised criteria, diagnosis of multiple sclerosis is still challenging and frequently takes several months or even years. Currently, contrast agent enhancement $T_1$-weighted imaging MRI is widely used to map inflammation caused by the BBB disruption during MS lesion formation. Quantitative DCE-MRI further has potential as a tool for identifying acute white matter lesions, monitoring disease progression as well as evaluating and designing treatment strategies specific to the preservation and repair of cortical GM.

The early diagnosis of MS would be of great benefit to patients in light of the potential for recurrence of attacks and progression of the disease. Drugs for the treatment of multiple sclerosis are now available which slow or prevent progression of the disease in many patients, and an early diagnosis would allow early intervention and could significantly improve the quality of life for many MS patients. The BBB has long been thought to play a key role in this by regulating leucocyte movement into the CNS. The BBB disruption and vascular changes are a prominent and early feature of MS pathogenesis and leads to the initiation of a CNS-specific immune response causing the pathological hallmarks of MS. The studies indicate that MS patients have a higher BBB permeability in the normal-appearing white matter when compared to healthy control subjects, and furthermore, when patients had recently experienced a clinical relapse the permeability increased significantly. Highly active inflammatory lesions have pronounced BBB leakage and therefore visibly enhance on $T_1$-weighted MRI after intravenous gadolinium administration.

FIGS. 3A, 3A1, 3B, and 3B1 show an example of detecting blood-tissue barrier breakdown of a patient with multiple sclerosis using $T_1$-weighted MR imaging. FIG. 3B depicts a brain image of a patient with MS acquired with 3D MP-RAGE at the isotropic resolution of 0.7 mm according to the optimal protocol of the present disclosure after the administration of 0.1 mmol/kg Gadavist. FIG. 3A depicts a brain image of a patient with MS acquired with 3D MP-RAGE at the isotropic resolution of 1.0 mm by a conventional routine protocol after the administration of 0.1 mmol/kg Gadavist. The total scan time is around 5 minutes for the optimal protocol of the present disclosure, and the conventional routine protocol. FIG. 3A1 depicts an enlarged view of a portion indicated as 3A1 in FIG. 3A. FIG. 3B1 depicts an enlarged view of a portion indicated as 3B1 in FIG. 3B. Several MS plaques are observed in FIG. 3B1, which are undetectable in FIG. 3A1. Quantitative analysis that MS plaque lesion-normal tissue contrast-to-noise increases 100% as the voxel size reduces from 1 mm³ to 0.35 mm³. This suggests that increasing the spatial resolution leads to increase the MS plague-tissue contrast, which is in a good agreement with Equation (8).

Example No. 3 Brain Tumor

An estimated 80,000 new cases of primary brain tumors will be diagnosed in the United States this year. Additionally around between 210,000 will be diagnosed with brain metastases, most often from lung cancer, breast cancer, and melanoma. Patients with primary malignant brain tumors and brain metastases often experience significant neurologic disability, impaired quality of life, and reduced survival. Though recent advances in treatment have improved outcomes, the relative 5-year survival rate following diagnosis of a primary malignant brain tumor is 35%, and the average survival of metastatic brain tumor patients remains at approximately six months. Clinically, brain tumor lesions are often diagnosed when they are sufficiently large to be detected on imaging. In later stage of tumor diagnosis, 1) the prognosis is extremely poor; 2) most potential therapies which may be effective at early stage fail to show their efficacy; and 3) the median survival is only about 3 months. Early stage diagnosis may lead to more treatment options to lengthen life of patients and increase quality of survival. Furthermore, early detection is beneficial to the development of new therapy agents and biomarkers developed for early detection can facilitate precise evaluation of response to therapy. Currently, contrast enhanced magnetic resonance imaging (CE-MRI) is considered as a gold standard technique for BM detection. Higher imaging resolution leads to better BM lesion detection sensitivity. However, contrast agent accumulation in lesions through blood-brain barrier (BBB) permeability limits the confident detection of CE-MRI to only larger tumors (around 5-10 mm in diameter or $10^7$-$10^8$ BM cells).

FIG. 4A shows an example of detecting blood-tissue barrier breakdown of a patient with brain tumor at the voxel spatial resolution of 1 mm³ at 3.0 Tesla MRI scanner after the administration of 0.1 mmol/kg Gadavist. FIG. 4B shows an example of detecting blood-tissue barrier breakdown of a patient with brain tumor at the voxel spatial resolution of 0.34 mm³ at 3.0 Tesla MRI scanner after the administration of 0.1 mmol/kg Gadavist. FIG. 4A1 depicts an enlarged view of a portion indicated as 4A1 in FIG. 4A. FIG. 4B1 depicts an enlarged view of a portion indicated as 4B1 in FIG. 4B. The brain tumor can be identified in both brain images. The brain image acquired with high spatial resolution in FIG. 4B demonstrates better tissue delineation within the brain tumor and improved tumor-tissue contrast, compared with the low-resolution image in FIG. 4A. The enhanced tumor-tissue contrast efficiency increases about 120%. It suggests that CE-MR with high resolution enables much smaller tumors to be detected that makes CE-MRI to be a powerful tool for early stage tumor detection. This result is consistent with Equation (8).

Figure 5A:
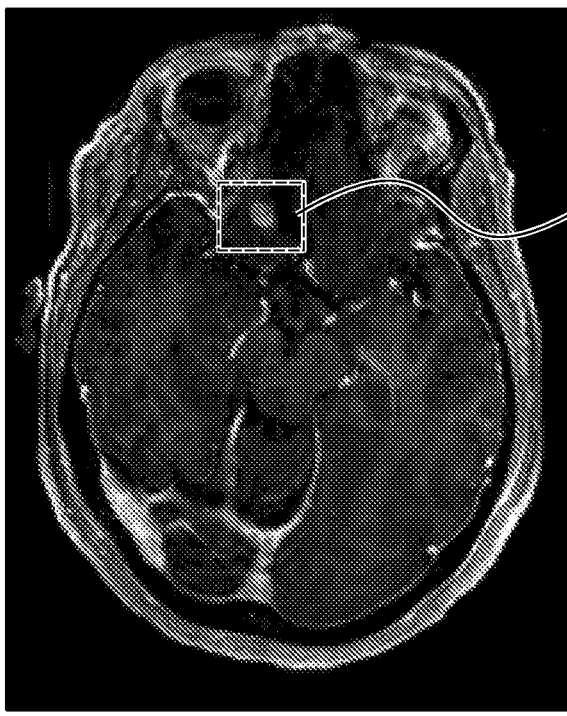
FIG. 5A shows an example of detecting blood-tissue barrier breakdown of a patient with brain tumor at the voxel spatial resolution of 0.34 mm$^3$ at 3.0 Tesla.
Figure 5A:
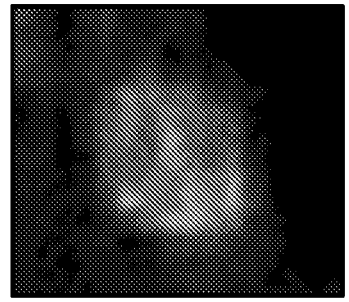
Figure 5B:
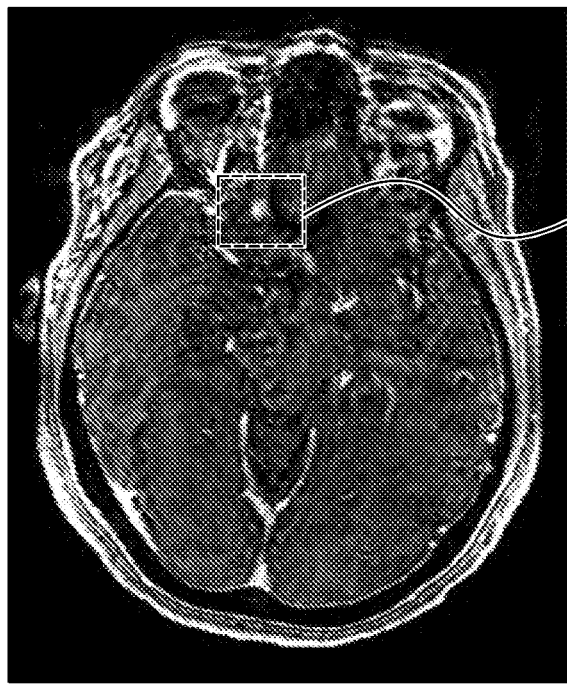
FIG. 5B shows an example of detecting blood-tissue barrier breakdown of a patient with brain tumor at the voxel spatial resolution of 0.125 mm$^3$ at 3.0 Tesla.
Figure 5B:
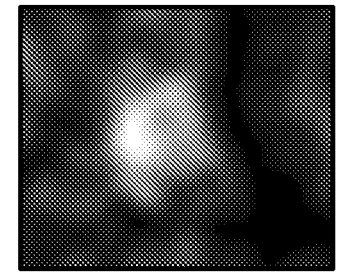

FIG. 5A shows an example of detecting blood-tissue barrier breakdown of a patient with brain tumor at the voxel spatial resolution of 0.34 mm³ at 3.0 Tesla MRI scanner after the administration of 0.1 mmol/kg Gadavist. FIG. 5B shows an example of detecting blood-tissue barrier breakdown of a patient with brain tumor at the voxel spatial resolution of 0.125 mm³ at 3.0 Tesla MRI scanner after the administration of 0.1 mmol/kg Gadavist. FIG. 5A1 depicts an enlarged view of a portion indicated as 5A1 in FIG. 5A. FIG. 5B1 depicts an enlarged view of a portion indicated as 5B1 in FIG. 5B. Quantitative analysis that tumor lesion-normal tissue contrast-to-noise increases 80% as the voxel size reduces from 0.34 mm³ to 0.125 mm³. This suggests that increasing the spatial resolution leads to increase the tumor lesion-tissue contrast, which is in a good agreement with Equation (8).

Example No. 4 Other Applications

Stroke is the fourth leading cause of death in the US with more than about 795,000 people in United States experience a new or recurrent stroke each year, and 137,000 people dying each year. Neuroinflammation leads to progressive damage in ischemic stroke. The BBB disruption occurs at 24-48 hours following ischemic stroke is a pathological mechanism that contributes to neuronal death. There is an urgent need to identify BBB disruption following stroke. The BBB disruption can enable the extravasation of low-molecular weight MRI contrast agents, leading to increased longitudinal relaxation rate and increased signal intensity in $T_1$-weighted images. DCE-MRI is considered to be the standard MRI approach for assessing permeability. However, DCE-MRI can only probe ischemic BBB disruption several hours after stroke onset and quantitative MRI measurement for BBB permeability takes time (at least 1 hour or longer), while in acute stroke care, every minute counts as ischemic brain tissue dies fast. In addition, limited access and low sensitivity are added concerns to DCE-MRI measurement.

Cerebral small vessel disease (CSVD) and dementia is a broad term that includes lesions in subcortical gray and white matter. It is associated with vascular cognitive impairment (VCI) and is regarded as a risk factor for dementia. The study indicated that the presence of cerebral small infarcts that can range from 50 µm to 15 mm in size and which are also considered a feature of CSVD. The sizes varying from 50 µm to a few mm is beyond the detection limit of current high-resolution MRI. The autopsy studies further indicate that small infarcts can be up to 43% of non-demented older individuals in cortical and subcortical areas of the brain. CSVD of the cerebral circulation are a major contributor to hemorrhagic stroke, dementias and other forms of neurological dysfunction. Recently, DCE-MRI is used to study cerebrovascular barrier function of older patients with clinical and MRI evidence of CSVD and find that the BBB disruption is more widespread in the patients.

There are a lot of works reported investigations of BBB in dementia patients showing significant BBB damage. The major drawback of these studies is that they only report at the end stage of the disease. Contrast agent MRI is the most widely adopted non-invasive imaging technique for evaluating BBB disruption, which is based on the use of MRI contrast agent. The MRI contrast agent can leak from the intravascular space to the interstitial space depending on the extent of BBB disruption. The contrast agent MRI methods can be divided in two groups: a) Dynamic susceptibility contrast enhanced MRI (DSC-MRI) based on $T_2$* changes and b) DCE-MRI based on $T_1$ images. Measurement of BBB disruption at its early stages of CSVD requires measuring low permeability values. This is a difficult challenge for contrast agent MRI.

Parkinson's disease is associated with a loss of neurons from the midbrain. Positron emission tomography indicated significantly elevated uptake of [$^{11}$C]-verapamil in the midbrain of PD patients relative to controls, and that a dysfunctional blood-brain barrier was a causative mechanism in PD.

FIG. 6A shows an example of detecting blood-tissue barrier breakdown of a patient with Parkinson's disease at the voxel spatial resolution of 0.512 mm$^3$ before contrast agent is administered. FIG. 6B shows an example of detecting blood-tissue barrier breakdown of a patient with Parkinson's disease at the voxel spatial resolution of 0.512 mm$^3$ after contrast agent is administered. FIG. 6A1 depicts an enlarged view of a portion indicated as 6A1 in FIG. 6A. FIG. 6B1 depicts an enlarged view of a portion indicated as 6B1 in FIG. 6B. In FIGS. 6A and 6B, contrast enhanced MRI experiment also indicated increased signal enhancement in the substantial nigra, compared with the tissue around the substantial nigra (such as Cerebellum). The increased signal enhancement indicated higher blood volume and/or BBB disruption in the substantial nigra. This may support that BBB disruption should be a good image biomarker for Parkinson's disease.

Finally, the therapies for many diseases, such as cancer and heart disease, neurodegenerative diseases, relate with the BBB. Although some effective treatments are available, most of those diseases remain undertreated. This is mainly because the BBB limits the drug delivery. As a result, only 5% of the more than 7000 small-molecule drugs available can currently treat central nervous system (CNS) diseases. Safe and non-invasive opening of the BBB is a significant challenge for the treatment. For example, MRI guided focused ultrasound to produce minimally invasive, safe, and transient opening of the BBB to increase BBB permeability for targeted drug delivery.

Alternatively or additionally, in some implementations, a contrast enhancement is used to describe the change of blood-brain barrier permeability in humans induced by drugs or techniques.

Specific implementations of the disclosed system and method are useful to illustrate its nature. These examples are non-limiting and are offered as exemplary only.

Alternatively or additionally, in some implementations, the lesion tissue can optionally be at least one of tumor, multiple sclerosis, Parkinson's disease, vascular cognitive impairment, chronic vascular disease but not limited to, inflammation disease, infection disease, stroke, traumatic nerve injury, vascular disease, Alzheimer's disease, dementia, schizophrenia, autism spectrum disorder and mood disorders.

Alternatively or additionally, in some implementations, a contrast enhancement is used to describe the change of blood-brain barrier permeability in humans induced by drugs or techniques. For example, highly focused ultrasound or laser-based approaches are used to open blood-brain barrier so that the therapy drug can cross blood-brain barrier to deliver to the local lesion.

Alternatively or additionally, in some implementations, the contrast agent can optionally be at least one physiologically acceptable paramagnetic substance, superparamagnetic substance, or ferromagnetic substance. Alternatively or additionally, in some implementations, the contrast agent can optionally be at least one of a magnetic small-molecule-based compound, a magnetic large-molecule-based compound, or a magnetic nanoparticle-based compound. Optionally, the contrast agent is administered by injection or orally.

Alternatively or additionally, the contrast agent is endogenous contrast agent which has lower toxicity than drugs and exogenous contrast media, for example, de-oxygenhemoglobin in blood.

Alternatively or additionally, in some implementations, the MRI sequence includes at least one of gradient echo, spin echo, gradient echo train, or spin echo train acquisition with or without magnetization preparation and/or specific tissue suppression. For example, fat saturation and/or CSF suppression.

Alternatively or additionally, qualitative differentiating healthy tissue and pathological tissue with blood-tissue barrier breakdown is performed visually.

An example system to detect small blood-tissue barrier breakdown or disruption is described herein. The example method can include (1) a receiver configured to acquire image data of the target region with a predetermined spatial resolution; (2) an administration of an exogenous or endogenous tracer into a subject; (3) a receiver configured to acquire at least one image data of the target region with the predetermined spatial resolution after administration of tracer; and (4) a processor configured to: differentiate pathological tissue with blood-tissue barrier breakdown from healthy tissue in the target region based on the acquired image data; and visualize or analyze the blood-tissue barrier breakdown of the pathological tissue based on the differentiation.

Alternatively or additionally, blood-tissue barrier is detected by at least one of, a magnetic resonance imaging (MRI) apparatus, a positron emission tomography (PET) apparatus, a computed tomography (CT) apparatus, and a single positron emission computed tomography (SPECT) apparatus.

Alternatively or additionally, the predetermined spatial resolution is less than 3.4 mm$^3$ for a voxel of the image data or 2.3 mm$^2$ for a pixel of the image data.

Alternatively or additionally, the predetermined spatial resolution is less than 1 mm$^3$ for a voxel of the image data or 1 mm$^2$ for a pixel of the image data.

Alternatively or additionally, the predetermined spatial resolution is less than 0.5 mm$^3$ for a voxel of the image data or 0.64 mm$^2$ for a pixel of the image data.

Alternatively or additionally, the predetermined spatial resolution is less than 0.35 mm$^3$ for a voxel of the image data or 0.5 mm$^2$ for a pixel of the image data.

Alternatively or additionally, the predetermined spatial resolution is less than 0.22 mm$^3$ for a voxel of the image data or 0.36 mm$^2$ for a pixel of the image data.

It should be understood that the above-described subject matter may also be implemented as a computer-controlled apparatus, a computer process, a computing system, or an article of manufacture, such as a computer-readable storage medium.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

In some embodiments, implementation of the disclosed methods may include generating one or more web pages for facilitating input, output, control, analysis, and other functions. In other embodiments, the methods may be implemented as a locally-controlled program on a local computer system which may or may not be accessible to other computer systems. In still other embodiments, implementation of the methods may include generating and/or operating modules which provide access to portable devices such as laptops, tablet computers, digitizers, digital tablets, smart phones, and other devices.

Thus, the invention provides, among other things, a method for estimating receiver sensitivity in a magnetic resonance (MR) system. Various features and advantages of the invention are set forth in the following.

The invention claimed is:

1. A method for detecting blood-tissue barrier breakdown or disruption, the method comprising:

acquiring first image data of a target region of a subject using a magnetic resonance imaging (MRI) apparatus, said MRI apparatus comprising an image reconstruction unit, with a predetermined spatial resolution, wherein the predetermined spatial resolution is less than 3.4 mm$^3$ for a voxel or 2.3 mm$^2$ for a pixel;

administrating exogenous or endogenous tracer into the subject;

acquiring at least one image data of the target region using the MRI apparatus with the predetermined spatial resolution after administration of the tracer;

quantitatively differentiating healthy tissue and pathological tissue with blood-tissue barrier breakdown in the target region using the MRI apparatus based on entire or part of the first image data and the at least one image data; and visualizing or analyzing the blood-tissue barrier breakdown of pathological tissue with the image reconstruction unit based on the differentiation, wherein the predetermined spatial resolution is determined by at least one fraction of blood-tissue barrier breakdown in a voxel or pixel.

2. The method of claim 1, wherein administrating the exogenous or endogenous tracer comprises:

administering the exogenous tracer by injection or orally; and administering the endogenous tracer by labeling or physiological changes.

3. The method of claim 1, wherein detection sensitivity of the blood-tissue barrier breakdown increases as the predetermined spatial-resolution increases.

4. The method of claim 1, wherein the predetermined spatial resolution is less than 1 mm$^3$ for a voxel of the image data or 1 mm$^2$ for a pixel of the image data.

5. The method of claim 1, wherein the predetermined spatial resolution is less than 0.5 mm$^3$ for a voxel of the image data or 0.64 mm$^2$ for a pixel of the image data.

6. The method of claim 1, wherein the predetermined spatial resolution is less than 0.35 mm$^3$ for a voxel of the image data or 0.5 mm$^2$ for a pixel of the image data.

7. The method of claim 1, wherein the predetermined spatial resolution is less than 0.13 mm$^3$ for a voxel of the image data or 0.25 mm$^2$ for a pixel of the image data.

8. The method of claim 1, wherein the at least one image data are acquired with at least one of dynamic contrast agent MRI, dynamic susceptibility contrast MRI, contrast enhanced MRI, and nuclear spin labelling MRI.

9. The method of claim 1, further comprising at least one of detecting a disease lesion, diagnosing a disease, performing treatment plan, monitoring disease therapy, or staging a disease.

10. The method of claim 1, wherein the detectable blood-tissue barrier breakdown of the pathological tissue is associated with early detection of various diseases, selected from the group consisting of tumor, multiple sclerosis, inflammation disease, infection disease, traumatic nerve injury, Alzheimer disease, Parkinson diseases, stroke, vascular disease, and various psychiatric disorders selected from the group consisting of: schizophrenia, autism spectrum disorder, and mood disorders.

11. The method of claim 1, further comprising determining a change of blood-tissue barrier permeability induced by drugs or techniques based on analysis of blood-tissue barrier breakdown of pathological tissue.

12. A system for detecting blood-tissue barrier breakdown or disruption, the system comprising:

a receiver configured to acquire image data of a target region of a subject using a magnetic resonance imaging (MRI) apparatus with a predetermined spatial resolution, wherein the predetermined spatial resolution is determined by at least one fraction of blood-tissue barrier breakdown in a voxel or pixel and the predetermined spatial resolution is less than 3.4 mm$^3$ for a voxel or 2.3 mm$^2$ for a pixel;

an image reconstruction unit; and a processor configured to:

receive, from the receiver, first image data of the target region of the subject before an exogenous or endogenous tracer is administered to the subject;

receive, from the receiver, at least one image data of the target region of the subject after the exogenous or endogenous tracer is administered into the subject;

quantitatively differentiate pathological tissue with blood-tissue barrier breakdown from healthy tissue in the target region based on entire or part of the acquired first image data and the acquired at least one image data using the MRI apparatus; and visualize or analyze the blood-tissue barrier breakdown of the pathological tissue based on the differentiation, using the image reconstruction unit.

13. The system of claim 12, wherein the predetermined spatial resolution is less than 1 mm$^3$ for a voxel of the image data or 1 mm$^2$ for a pixel of the image data.

14. The system of claim 12, wherein the predetermined spatial resolution is less than 0.5 mm$^3$ for a voxel of the image data or 0.64 mm$^2$ for a pixel of the image data.

15. The system of claim 12, wherein the predetermined spatial resolution is less than 0.35 mm$^3$ for a voxel of the image data or 0.5 mm$^2$ for a pixel of the image data.

16. The system of claim 12, wherein the predetermined spatial resolution is less than 0.13 mm$^3$ for a voxel of the image data or 0.25 mm$^2$ for a pixel of the image data.

* * * * *